United States Patent [19]
de la Cruz

[11] 3,961,524
[45] June 8, 1976

[54] METHOD AND APPARATUS FOR DETERMINING ROCK STRESS IN SITU

[75] Inventor: Rodolfo V. de la Cruz, Madison, Wis.

[73] Assignee: The United States of America as represented by the Secretary of the Interior, Washington, D.C.

[22] Filed: May 6, 1975

[21] Appl. No.: 574,992

[52] U.S. Cl. .............................................. 73/88 E
[51] Int. Cl.² ........................................ E21B 49/00
[58] Field of Search ................ 73/88 E, 84, 94, 151

[56] References Cited
UNITED STATES PATENTS

| | | | |
|---|---|---|---|
| 3,446,062 | 5/1969 | Goodman et al. | 73/88 E UX |
| 3,600,938 | 8/1971 | Waddell | 73/88 E |
| 3,796,091 | 3/1974 | Serata | 73/88 E |

*Primary Examiner*—Jerry W. Myracle
*Attorney, Agent, or Firm*—Gersten Sadowsky; Donald R. Fraser

[57] ABSTRACT

Rock stress in a borehole wall is determined in situ by obtaining an initial strain reading of the wall, relieving the strain by fracturing the wall from within the borehole with a hydraulic jack, obtaining a relieved strain reading, and using the two strain readings to determine stress. The jack comprises a pair of diametrically opposed loading members for applying a self-equilibrating pair of forces to opposite quadrants of the wall, and a pair of diametrically opposed piston members for impressing a set of friction strain gauges against the remaining quadrants. The piston members are pivotally mounted to the jack to allow the strain gauges to conform to the shape of the wall. The jack is first located at the preselected region of the borehole and the loading members are separated until they contact the wall to stabilize the jack in the borehole. The pistons are operated to move the strain gauges into firm abutment with the wall to obtain the initial strain reading. The loading members are then further separated to fracture the wall for strain relief, and the relieved strain reading is obtained. Finally, the loading members and pistons are withdrawn from the wall for relocating the jack to another region of the borehole. The initial and relieved strain readings are used to determine the initial state of stress of the rock and the strain of the rock measured as a function of the loading of the borehole wall is used to determine the value of Young's Modulus of the rock for an assumed value of Poisson's Ratio.

14 Claims, 11 Drawing Figures

METHOD AND APPARATUS FOR DETERMINING ROCK STRESS IN SITU

BACKGROUND OF THE INVENTION

The present invention relates to measurement of stress in rock, and more particularly to a jack fracturing method and apparatus for measuring the natural state of stress of rock, as well as the value of Young's Modulus for an assumed value of Poisson's Ratio of the rock.

In structural engineering, it is imperative that the natural state of stress in rock masses at a preselected depth be known for rational design of earth supported structures. Knowledge of the in situ earth stresses is also of importance in the design of tunnels, mines, dams and other subterranean structures.

The present techniques for measuring the state of stress of rock in situ include: (a) the rock property method, (b) the rock strain method and (c) the rock fracture method.

In the rock property method, a property of the rock material, such as sound propagation velocity, is measured, and the property is correlated to rock stress. However, in practice, only two normal propagation velocities are detectable at a preselected region in the rock, and the data derived therefrom are inadequate to determine the six independent components of stress that exist in the general case.

In the rock strain method, a rock segment is stress relieved in situ by cutting it free from its surroundings. This is typically done by drilling a strain relief borehole adjacent a primary borehole, and the change of strain of the rock segment between the boreholes is measured. The change of strain is related to the initial state of stress of the rock and can be determined using tensor analysis. The rock strain method is widely used because it provides the magnitudes as well as directions of the principle stresses of the rock. However, the rock strain method is impracticable for deep subterranean regions stress determination because the strain-relieving borehole must have a precise orientation with respect to the primary borehole. A technique known as overcoring is commonly used whereby a tubular strain-relieving borehole is cut coaxially to the primary borehole to relieve the stress on the primary borehole wall. Obviously, alignment of the two boreholes is critical and the rock strain method is practical only in relatively shallow regions.

On the other hand, the rock fracture method is somewhat practical for deep borehole strain determination. There, a non-compressible fluid is sealed into an enclosed portion of the borehole. The hydraulic pressure in the sealed portion is increased using a hydraulic pump until the wall of the enclosed portion of the borehole is caused to fracture. The magnitude of the hydraulic pressure required to fracture the borehole wall is determinative of two components of stress. But since nine stress components exist in the general case, the borehole must be oriented in a principle stress direction in order to eliminate the shear stress components. Precise orientation of the borehole is somewhat difficult to achieve in deep borehole regions, and the measurements are very sensitive to the porosity of the rock. Variations in rock porosity and misorientation of the borehole with respect to a principle stress direction diminish the accuracy of the stress measurements.

It is well known that stress and strain are related to each other in a material as a function of Young's Modulus, (modulus of elasticity), E, for a given value of Poisson's ratio $\mu$. Typically, E is measured in rock by extracting a sample of the rock from the region of interest and then studying the stress-strain behavior of the sample. Thus, determination of the natural state of stress of the rock requires two separate procedures (measurement of strains in situ, and determination of E) which are time consuming and expensive.

Accordingly, one object of the present invention is to provide a new and improved method and apparatus for measuring the natural state of stress of rock in situ.

Another object of the invention is to provide a new and improved method and apparatus for measuring rock stress as well as other characteristics of the rock, such as Young's Modulus in situ with a single procedure.

A further object of the invention is to provide a new and improved method and apparatus for measuring rock stress at both shallow and deep subterranean regions, wherein orientation of the borehole is not critical.

A further object of the invention is to provide a new and improved method and apparatus for measuring rock stress in a borehole wherein the wall of the borehole is fractured for strain relief.

An additional object of the invention is to provide a new and improved method and apparatus for measuring rock strain wherein a self-aligning apparatus is positioned in the borehole to fracture the wall of the borehole for stress relief, and to obtain initial and relieved strain readings of the rock.

An additional object of the invention is to provide a new and improved, self-contained and reusable instrument for measuring the natural stress of rock in a preselected subterranean region.

Yet another object of the present invention is to provide a new and improved instrument, comprising an hydraulic jack for applying self-equilibrating forces to opposite quadrants of the borehole, and measuring values of strain of the rock on the remaining quadrants.

SUMMARY OF THE INVENTION

Briefly, according to the present invention, the natural state of stress of rock at a pre-selected region in a borehole is determined by obtaining an initial strain reading of the wall of the borehole at the pre-selected region, radially fracturing the wall with a borehole jack for stress relief, and then obtaining a relieved (de-stressed) strain reading. The initial strain and relieved strain readings are used to determine the state of stress of the rock using conventional tensor analysis. The value of Young's Modulus is also determined by continuously monitoring rock strain during jack loading of the borehole wall.

More particularly, a borehole is first drilled into the rock mass extending into the pre-selected region, which may be subterranean. Alternatively, the pre-selected region may be located in a pre-existing borehole. In either case, a rod-shaped borehole jack is lowered into the borehole and positioned at the pre-selected region.

The jack, which is preferably hydraulic, comprises a pair of diametrically opposed loading members (one of the members is movable, the other is stationary) attached to curved bearing plates for applying a self-equilibrating pair of forces to opposite quadrants of the borehole, and a pair of diametrically opposed pistons for impressing friction strain gauges against the remaining quadrants.

With the jack located at the pre-selected region in the borehole, the loading members are initially separated until the bearing plates seat against opposite quadrants of the wall of the borehole. The loading members stabilize the jack in the borehole but do not yet substantially load the borehole wall.

The friction strain gauges, attached to the heads of the pistons, are moved into firm abutment with the remaining quadrants of the borehole to obtain strain readings of the wall. Then, while continuously monitoring the output of the strain gauges, the loading members are further separated to load the borehole wall until radial fractures of substantial length are created adjacent the strain gauges. By keeping the fractures open with the bearing plates, i.e., by not unloading the jack, the rock in the vicinity of the fractures is relieved (de-stressed), and final (relieved) strain readings, are obtained from the strain gauges.

The magnitude of the initial strain of the rock is the negative equivalent of the difference between the initial and final readings of the strain gauges. Knowing the magnitude of the initial strain of the rock and the value of Young's Modulus, the initial (natural) state of stress of the rock is computed using conventional structural analysis. The value of Young's Modulus for an assumed value of Poisson's Ratio of the rock is determined during the procedure by recording the output of the strain gauges as a function of jack loading, prior to fracture.

After the strain readings are obtained, the pistons, carrying the strain gauges, as well as the loading members are retracted, releasing the jack from the wall of the borehole. This readies the jack for another set of strain readings elsewhere in the borehole, or for removal therefrom.

Two independent hydraulic systems are incorporated in the jack. The first hydraulic system includes a first longitudinal bore in communication with a plurality of pressure pistons forming the movable loading member. Hydraulic pressure, applied to the first bore, causes the pressure pistons to expand separating the movable bearing plate from the stationary bearing plate to load the borehole wall. The amount of loading of the wall is a function of the hydraulic pressure applied to the first longitudinal bore.

The second hydraulic system comprises a second longitudinal bore in communication with a pair of opposed pistons carrying the friction strain gauges. Hydraulic pressure, applied to the second longitudinal bore, causes the pair of pistons to extend outwardly from the jack until they firmly abut the wall of the borehole. The pistons, carrying the strain gauges, are pivotally mounted to the jack so that the strain gauges automatically conform to the shape of the wall.

The heads of the pair of pistons have a radius of curvature equal to that of the borehole and may extend angularly up to 90° around the wall of the borehole. The friction strain gauges, distributed on the piston heads, are oriented at different angles with respect to the wall of the borehole so that all the necessary strain component readings are obtained.

The friction strain gauges are maintained in firm abutment with the borehole wall during the strain readings, but are not bonded to the wall. The gauges are not left behind on the borehole wall after each strain reading as in the prior art, and the prior requirement of withdrawing the apparatus from the borehole after each reading is obviated. And since the friction strain gauges are resuable, the cost of taking strain readings in situ is reduced.

Thus, another object of the present invention is to provide a new and improved method and apparatus for determining the state of stress of rock at different pre-selected regions in a borehole, wherein the strain gauges are not bonded to the borehole wall.

It is another object of the present invention to provide a new and improved method and apparatus for determining stress in rock at several different pre-selected regions of a borehole, wherein successive strain measurements are obtained without removing the instrument from the borehole.

It is another object of the present invention to provide a new and improved method and apparatus for determining stress of rock masses, wherein only a single set of strain gauges is required for performing a plurality of strain measurements at different, pre-selected regions of a borehole.

Still other objects and advantages of the present invention will become readily apparent to those skilled in this art from the following detailed description, wherein I have shown and described only the preferred embodiment of the invention simply by way of illustration of the best mode contemplated by me of carrying out my invention. As will be realized, the invention is capable of other and different embodiments, and its several details are capable of modification in various obvious respects, all without departing from the invention. Accordingly, the drawings and description are to be regarded as illustrative in nature, and not as descriptive.

DETAILED DESCRIPTION OF THE PREFERRED EMBODIMENT

Figure 1:
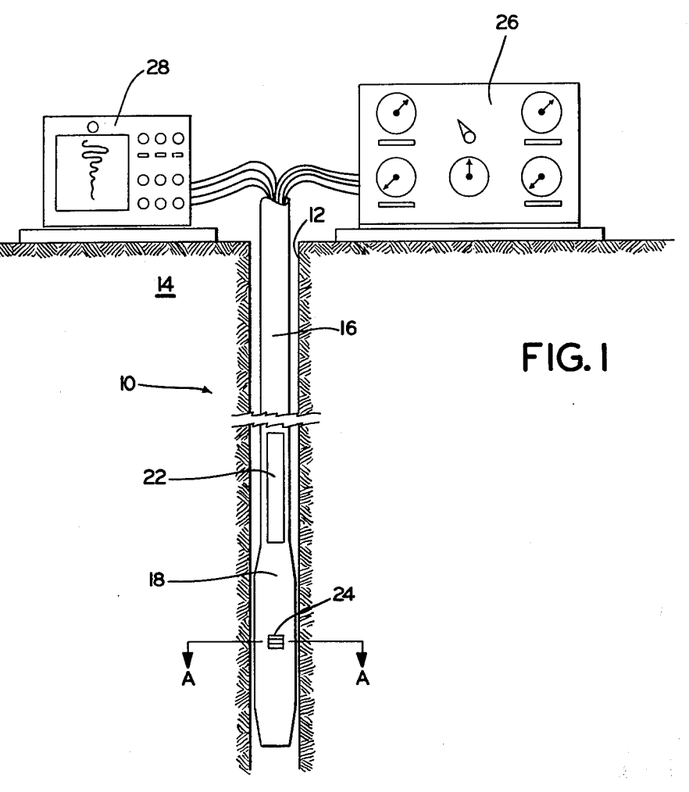
FIG. 1 is a schematic diagram of the hydraulic jack system according to the present invention, positioned within a borehole.

Referring to FIG. 1, the apparatus of the present invention, generally designated by the numeral 10, is shown inserted axially into a test borehole 12 cut into a subterranean medium 14 to be evaluated.

As an overview, apparatus 10 is generally rod-shaped and comprises a drill rod or casing upper portion 16, a jack portion 18 and a conventional orientation device 22. Orientation device 22, which typically includes a camera and combination compass-inclinometer, measures the orientation of the apparatus 10 with respect to the principle stress axes of the rock. Jack portion 18, according to the invention, includes a hydraulic jack for fracturing the wall of borehole 12, and a friction gauge module 24 for measuring the strain of the wall borehole, as will be described in detail later.

Apparatus 10 is controlled, from ground level, by an operation control panel 26 which monitors and controls the depth and orientation of apparatus 10, and controls the operation of jack portion 18 and friction gauge module 24. Also located at ground level is a strain gauge recorder 28, which may be a conventional visicorder, for reading and recording the output of the strain gauge module 24 as a function of jack loading of the borehole wall.

In accordance with the present invention, the natural state of stress of rock at a pre-selected region, is determined by drilling a borehole into the earth extending down to the pre-selected region, obtaining an initial strain reading of the rock at the pre-selected region, relieving the rock of stress at the pre-selected region by fracturing the wall of the borehole, and, while maintaining open the fracture, obtaining a stress relieved (de-stressed) strain reading of the rock. As will be discussed in more detail later, the initial strain and de-stressed strain readings are used to determine the initial state of stress of rock at the pre-selected region. Also the strain of the borehole wall as a function of the loading thereof prior to fracturing is determinative of the value of Young's Modulus of the rock (for an assumed value of Poisson's Ratio).

Referring to FIGS. 2A–2D, summarizing the operation of apparatus 10, there are shown four simplified cross-sectional views of the jack portion 18 taken along the line A—A of FIG. 1. Jack portion 18, shown operating within borehole 12, includes a pair of borehole loading members 30 and 32 for applying a self-equilibrating, uniaxial pair of forces F (FIG. 2C) to opposite quadrants 12a and 12b of borehole 12. Curved bearing plates 30a and 32a are attached respectively to the ends of loading members 30 and 32 for contacting the borehole wall. Bearing plates 30a and 32a have a radius of curvature corresponding to the size of the borehole for which apparatus 10 is used. Preferably a variety of different sizes of interchangeable bearing plates are provided so that the apparatus 10 can be used with boreholes of any size. As will be described in detail later, one of the loading members 30 is movable; the other loading member 32 is stationary.

Jack portion 18 further includes a pair of oppositely movable piston assemblies 23a and 23b, supporting sets 24a and 24b of conventional friction strain gauges for obtaining strain readings of the remaining quadrants 12c and 12d of the borehole wall. Unlike the stressing members 30 and 32, pistons 23a and 23b are each movable.

Figures 2, 2A:
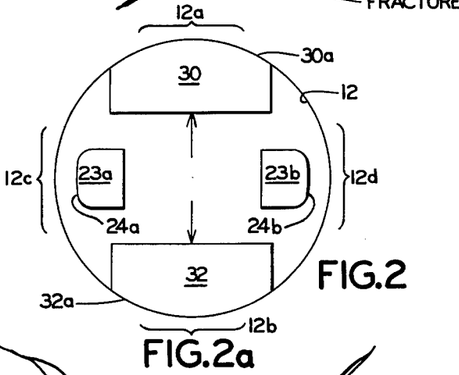
FIGS. 2A–2D are schematic cross-sectional views of the hydraulic jack illustrating the operation of the loading members and strain gauges taken along the line A—A in FIG. 1.
Figure 2B:
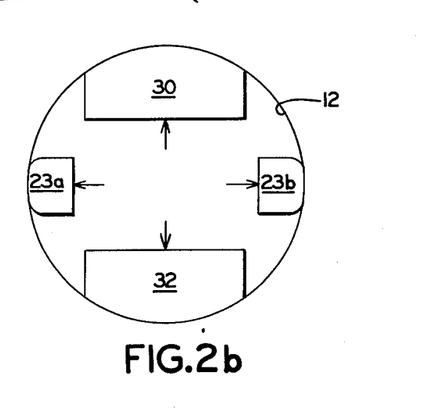

The method of the invention comprises five basic steps, viz: (a) locating the jack apparatus 10 at a preselected region within the borehole wall 12; (b) separating loading members 30 and 32 until they come in contact with opposite quadrants 12a and 12b of the borehole wall in order to stabilize the jack (FIG. 2A); (c) moving strain gauges 24a and 24b into firm abutment with the remaining quadrants 12c and 12d of the borehole wall for obtaining an initial strain reading (FIG. 2B); (d) further separating loading members 30 and 32 until they fracture the wall of borehole 12 (FIG. 2C) while monitoring the outputs of strain gauges 24a and 24b (note fractures), and, while maintaining open the fractures, obtaining a relieved strain reading from the output of the strain gauges; and (e) retracting the loading members 30 and 32 and the strain gauges 24a and 24b (FIG. 2D) thereby readying the apparatus for obtaining a set of strain readings elsewhere in the borehole, or for removing the apparatus therefrom. The initial state of stress of the rock is determined from the initial and final strain gauge readings using conventional tensor analysis as will be discussed in detail in the following section.

THEORY AND METHOD OF THE INVENTION

The present invention is based on the principle that rock fracturing relieves the stresses applied to rock masses in the vicinity of the fracture. Although a closed form analytical solution to the borehole fracturing problem is not available, strain relief in proximity to the fracture can be shown by either consideration of the boundary conditions and external forces applied at the borehole, or by conventional numerical approximation techniques used in structural analysis.

While a three-dimensional analysis must be made on the borehole fracturing problem in the general case, examination of the boundary conditions of a borehole shows that the three-dimensional problem can be reduced to a two-dimensional (plane) strain problem when the load stress applied to the borehole wall by the jack is at least four to six borehole diameters long.

Figure 3:
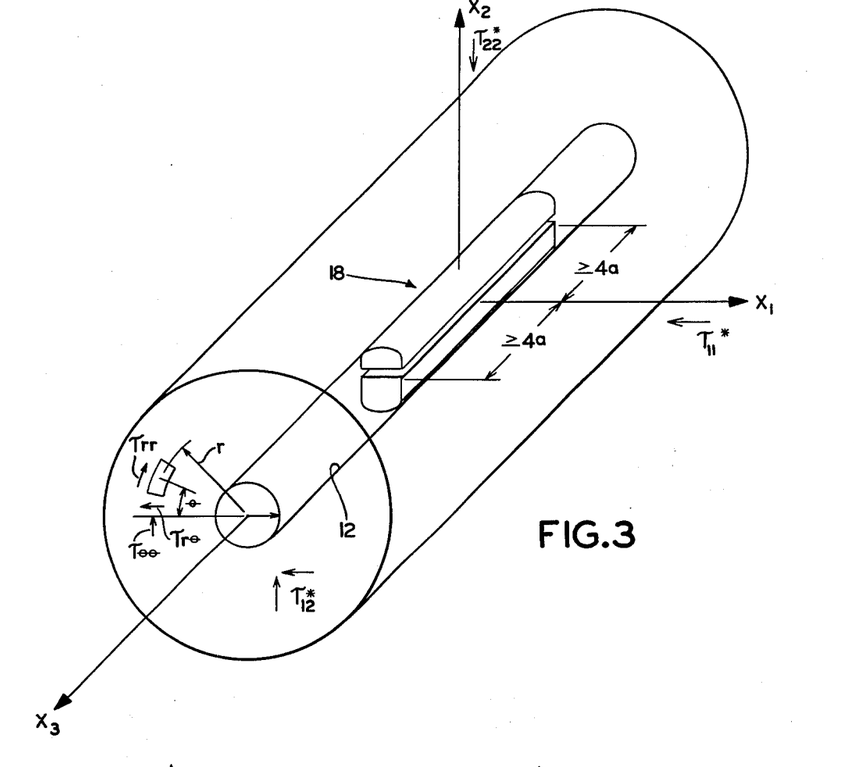
FIG. 3 is a schematic representation of the jack positioned within a borehole for explaining the theory of the invention.

Referring to FIG. 3, showing a schematic representation of a borehole 12 enclosing jack 18, the jack and borehole are oriented in three-dimensional space along the axis $X_3 = 0$. In the central portion of the jack 18 where strain relief measurements take place (see FIG. 1), the entire length of the borehole appears loaded by the jack. Since the natural state of stress of the rock is considered uniform for the purpose of analysis, and the length of the jack is assumed to be substantially greater than the diameter of the borehole, the following equations can be written:

$$\frac{\delta \tau_{ij}}{\delta X_3} = 0, \; i, j = 1, 2, 3...$$

$$\frac{\delta U_1}{\delta X_3} = \frac{2 U_2}{2 X_3} = 0$$

$$\frac{\delta \epsilon_{33}}{\delta X_3} = 0$$

at $X_3 = 0$ where $\epsilon_{33}$ is the axial strain, $\tau_{ij}$ is an arbitrary stress component, and $U_1$ and $U_2$ are deformations respectively applied along the axes $X_1$ and $X_2$ directions.

Thus, the problem reduces to a two-dimensional strain analysis, and conventional two-dimensional methods of analysis are adequate for determining the state of stress in the rock masses after obtaining initial and final strain readings.

Still referring to FIG. 3, the original state of stress of the rock is defined by two normal stress components $\tau_{11}*$ and $\tau_{22}*$, and one shear stress component, $\tau_{12}*$. With the introduction of the borehole along the $X_3$ axis, the stresses $\tau_{ij}{}^I$ in the immediate vicinity of the borehole are modified to new values that are functions of (1) the initial stress, $\tau_{ij}*$, and (2) their distances and orientations $r$, $\theta$, with respect to the borehole. Accordingly, the following equation can be written.

$$\tau_{ij}' = f(\tau_{ij}*, r, \theta, a) \quad (1)$$

where:
$\tau_{ij}*$ = original stress field,
$a$ = radius of the borehole, and
$r, \theta$ = coordinates of an arbitrary stress measurement.

In borehole fracturing, one is concerned with only the stresses at the periphery or wall of the borehole and, for convenience, the stresses are described in cylindrical coordinates as follows:

$$\tau_{rr}' = \tau_{r\theta}' = 0.$$
$$\tau_{\theta\theta}' = (\tau_{11}* + \tau_{22}*) - 2(\tau_{11}* - \tau_{22}*)\cos 2\theta - 4\tau_{12}* \sin 2\theta \quad (2)$$

Since $\tau_{\theta\theta}'$ is the only non-zero stress component at the periphery of the borehole, it only is required to determine values of $\tau_{\theta\theta}'$ at three different orientations for the two-dimensional stress system to be completely defined. These values are obtained directly from the tangential strain relief measurements at these points, obtained from the strain gauge module 24 (FIG. 1). Since, as aforementioned, the system is a generalized two-dimensional strain system, the relationship between stress and strain is expressed as:

$$\tau_{\theta\theta}' = \frac{E}{1-\mu^2} \epsilon \quad (3)$$

where:
E = Young's Modulus, and
$\mu$ = Poisson's Ratio.

From Equations (2) and (3), the measured tangential strain is related to the original stress field as follows:

$$\epsilon_{\theta\theta} = \frac{1-\mu^2}{E}[(1-2\cos2\theta)\tau_{11}* + (1 + 2\cos2\theta)\tau_{22}* - 4(\sin2\theta)\tau_{12}*] \quad (4)$$

These relations may be expressed in matrix form as:

$$[\epsilon] = [A][\tau] \quad (5)$$

where:
$[\epsilon]$ = column matrix of initial strain components determined from the strain gauge readings,
$[A]$ = 3×3 matrix of stress component coefficients, and
$[\tau]$ = column matrix of determined stress components.

Solving Equation (5) for the stress components gives:

$$[\tau] = [B][\epsilon] \quad (6)$$

where:
$[B] = [A]^{-1}$.

Thus, according to the present invention, initial strain components are read from the strain gauge module 24 at three predetermined angles, $\theta$, and the components of the initial stress of the rock are calculated from Equation (6). As mentioned, each initial strain component $\epsilon_{\theta\theta}$ is the negative equivalent of the difference between the final strain reading and the initial strain reading from strain gauge module 24.

For example, assuming that strain readings are obtained at $\theta = 0$, $\theta = \pi/4$, and $\theta = \pi/2$, [A] and [B] are calculated respectively from Equations (4) and (6) as follows:

$$[A] = \frac{1-\mu^2}{E} \begin{bmatrix} -1 & 3 & 0 \\ 3 & -1 & 0 \\ 1 & 1 & 4 \end{bmatrix}$$

$$[B] = \frac{1-\mu^2}{E} \begin{bmatrix} 0.125 & 0.375 & 0 \\ 0.375 & 0.125 & 0 \\ 0.125 & 0.125 & -0.25 \end{bmatrix}$$

Figure 4:
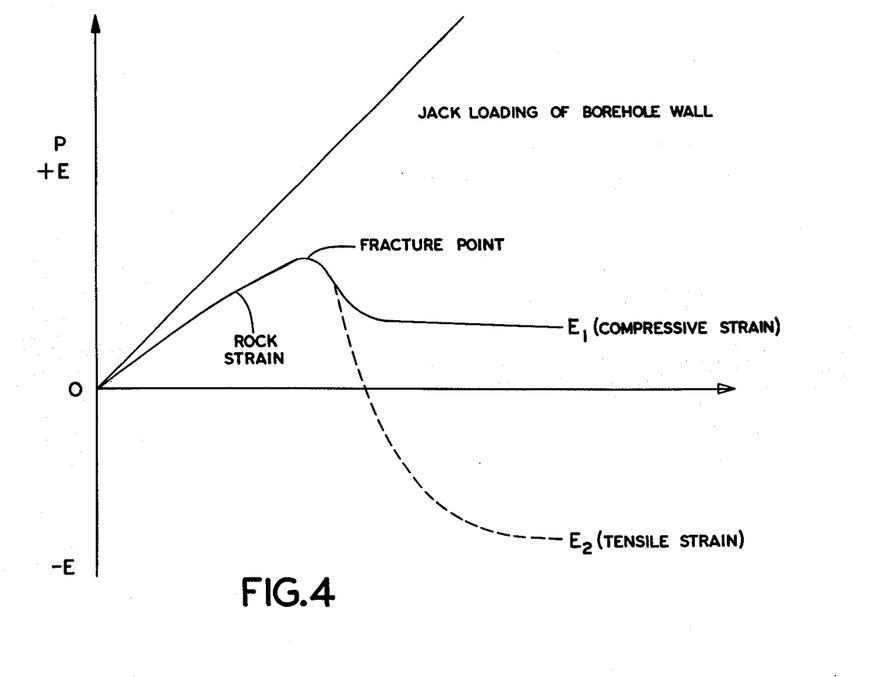
FIG. 4 is a graph showing a typical output signal generated by the strain gauges as a function of borehole loading by the hydraulic jack.

The value of Young's Modulus E for an assumed value of Poisson's Ratio $\mu$ is obtained from the outputs of the strain gauge sets 24a and 24b during loading of the borehole wall but before the fracturing thereof. The method of determining the value of Young's Modulus from the stress-strain characteristic of the rock, shown graphically in FIG. 4, is conventional and will not be described herein. However, it is noted that as one important aspect of the present invention, the value of Young's Modulus, as well as the initial state of stress of the rock, is determined during one set of measurements taken during one procedure without removing the apparatus 10 from the borehole. This is advantageous over prior systems wherein the value of Young's Modulus and the initial state of stress of the rock had to be separately determined and could not be completed in one procedure.

In the practice of the invention, loading members 30 and 32 are caused to apply a self-equilibrating pair of forces F to opposite quadrants of borehole 12 to increase the strain of the rock until the wall of the borehole fractures. When the wall fractures, the strain of the rock in proximity to the fractures is relieved. This phenomenon is illustrated in the graph of FIG. 4 for both compressive and tensile initial strain. The upper line represents the load stress applied by the loading members 30 and 32 of jack 18 to the opposite quadrants of the borehole. As the loading of the borehole wall is increased, strain of the rock, shown by the lower line, increases substantially linearly until the wall of the borehole fractures. Then the strain of the rock suddenly decreases to a constant value $\epsilon_1$ for compressive strain, or $\epsilon_2$ for tensile strain.

Figure 2C:
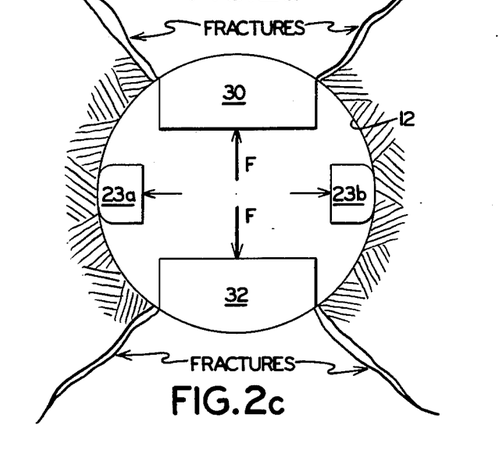
Figure 2D:
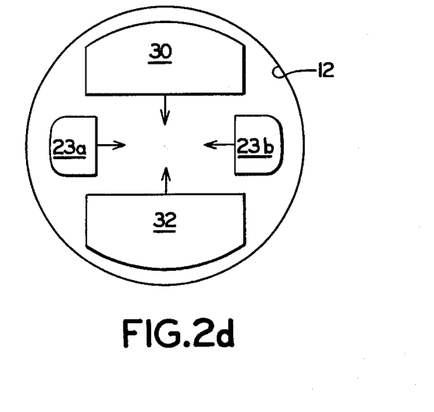

Referring to FIG. 2C, it is seen, by the crosshatched portion of the rock, that only a fraction of the rock is completely relieved of stress. Portions of the rock at the periphery of the borehole and adjacent the fracture are completely strain relieved, while other portions only partially relieved, and still other portions may be even further stressed. However, since the rock in the vicinity of a fracture is always completely relieved when the lengths of the fractures are substantial, obtaining rock strain readings at quadrants 12c and 12d (FIG. 2A) after the rock is fractured provides an accurate and reliable measurement of de-stressed strain of the rock.

That the rock in the vicinity of the fracture near the periphery of the borehole wall is completely de-stressed can be proved mathematically and demonstrated empirically; however, referring again to FIG. 2C, it can be seen that the cross-hatched portions of the rock at quadrants 12c and 12d of the borehole are free from the surrounding rock masses, particularly near the periphery or wall of the borehole. Thus, quadrants 12c and 12d, separated from the loaded quadrants 12a and 12d, at the borehole 12, stand as free boundaries, i.e., there are no external forces acting on them.

As aforementioned, it is necessary that the fractures formed in the borehole wall be substantial in length in order to insure complete strain relief even in portions of the wall adjacent the periphery of the borehole, and that the fractures be maintained open while the relieved strain reading is obtained. In practice, the output of the strain gauges 24 are monitored to determine when the fractures are substantial in length by slightly increasing the load on the borehole wall after the strain reading has stabilized beyond the fracture point (see FIG. 4), and maintaining open the fractures by not unloading the jack.

The fractures are shown as extending radially from the tips T of the bearing plates of members 30 and 32 (FIG. 7); however, it is understood that the fractures can originate from other portions of the plates depending on the surface configuration of the plates, the rock materials, and natural state of stress, thereof. For example, using the bearing plate configuration shown in FIG. 7, I have observed that in artificial rock mass formed of plaster-celite or concrete, a uniaxial pair of horizontal fractures (not shown) in line with strain gauges 24 develop in the wall of the borehole 12 as the wall is overloaded by the loading members 30 and 32.

Figure 7:
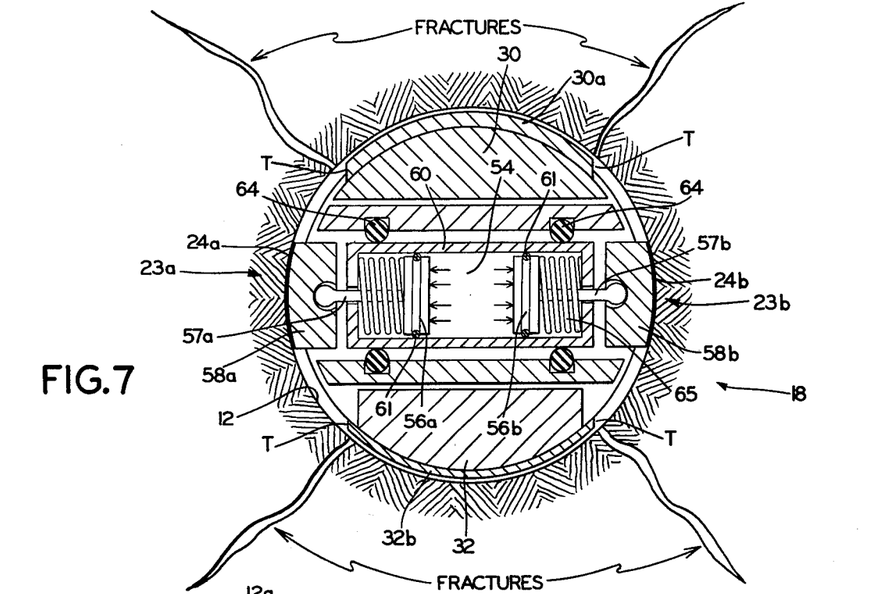
FIG. 7 is a cross-sectional view of the hydraulic jack taken along the line A—A in FIG. 1.

To recapitulate, in the practice of the present invention, the natural state of stress of rock at a pre-selected region of a borehole in situ, is determined by positioning jack 18, determined by the output of a conventional orientation device 22, at the pre-selected region in the borehole, and expanding loading members 30 and 32 until they contact the wall of the borehole for stabilization of the jack. Then friction strain gauge sets 24a and 24b, mounted on movable pistons 23a and 23b, are moved into firm abutment with the remaining quadrants of the borehole wall, and an initial strain reading of the wall is obtained from the strain gauges. The loading members 30 and 32 are further expanded to increase the strain on quadrants 12a and 12b of the wall until the wall fractures radially as shown in FIG. 2C and FIG. 7. The fractures are maintained open, i.e., by not unloading the jack, and a final (relieved or de-stressed) strain reading is obtained from the outputs of strain gauge sets 24a and 24b. The initial strain of the borehole wall is computed using the following equation:

$$\epsilon_{\theta\theta} = -(\epsilon_i - \epsilon_f) \qquad (7)$$

where
$\epsilon_i$ = initial strain reading, and
$\epsilon_f$ = final strain reading.

The initial (natural) state of the stress of the rock is then determined by applying three values of $\epsilon305$ taken at three different values of $\theta$ to Equation (6) above. The computations may, if desired, be performed with a programmed general purpose digital computer included in control panel 26 (FIG. 1) or located elsewhere. Programs for computing the components of strain in accordance with the aforementioned equations are known to skilled digital computer programmers, and are not set forth herein.

APPARATUS OF THE INVENTION

Figure 5:
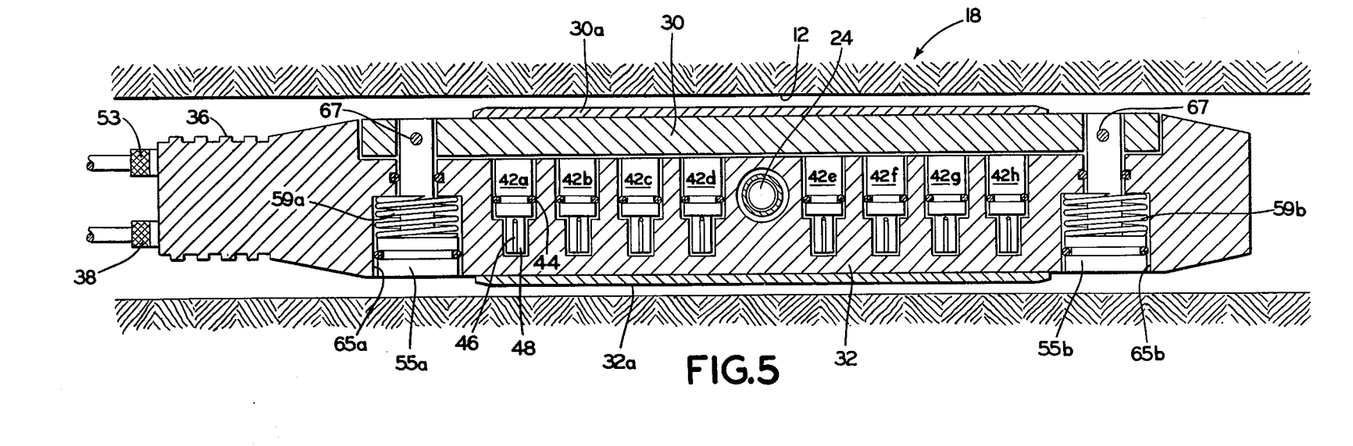
FIG. 5 is a longitudinal cross-sectional view of the hydraulic jack taken along the plane of the loading members.

Referring now to FIGS. 5–8, the jack portion 18 of the instrument 10 will be described in detail. Referring first to FIG. 5, there is shown a longitudinal cross-section of the jack 18 taken along the plane of loading members 30 and 32 (perpendicular to the axis of strain gauge module 24). As shown, hydraulic jack 18 is substantially rod-shaped and adapted to mount to a drill rod or casing 16 (FIG. 1) at threaded end portion 36.

Hydraulic jack 18 comprises three independent hydraulic systems (see FIG. 8) supplied by a single hydraulic pressure source 69. A first hydraulic system 70 receives hydraulic fluid from source 69 through control module 26a (a part of control panel 26), a first coupling 38 and communicating through line 40 with a serially connected plurality of pressure pistons 42a–42h operating the movable loading member 30. Hydraulic high pressure O-ring seals 44 (FIG. 5) prevent hydraulic oil from leaking around the pressure pistons 42a–42h. Small T-shaped passageways 46 (FIG. 5) and clearance around the stems 48 of the pistons 42a–42h distribute hydraulic oil under each piston.

The movable bearing plate or shoe 30a (see also FIGS. 2A and 7) is attached to the loading member 30 that is, in turn, attached to the ends of pressure pistons 42a–42h. These pistons, when actuated by hydraulic pressure, separate the movable bearing plate 30a from the stationary bearing plate or shoe 32a until the plates contact opposite quadrants of the borehole wall. More particularly, as pressure is applied to line 40 the movable bearing plate 30a moves outwardly from its rest position, shown in FIG. 5, until it contacts one quadrant of the borehole wall 12. Then, as the pressure is increased the plates 30a and 32a further separate by the outward movement of pressure pistons 42a–42h, until the stationary bearing plate 32a is caused to come into contact with the opposite quadrant of the wall. The radii of curvature of bearing plates 30a and 32a are identical to each other and have such a magnitude to cause the plates to conform to the borehole wall.

The amount of stress or loading applied to the borehole wall is determined by the hydraulic pressure supplied to the pressure pistons 42a–42h through line 40. Only enough pressure is initially supplied through control module 26a to the pressure pistons 42a–42h to cause the bearing plates 30a and 32a to contact the borehole wall for stabilizing the jack 18. In a similar manner, the strain gauge sets 24a and 24b are impressed against opposite quadrants of the borehole wall by supplying pressure to the second hydraulic system 71. Then, as will be seen in further detail below, hydraulic pressure applied to pressure pistons 42a–42h through line 40 is gradually increased until the wall of the borehole fractures.

Figure 6:
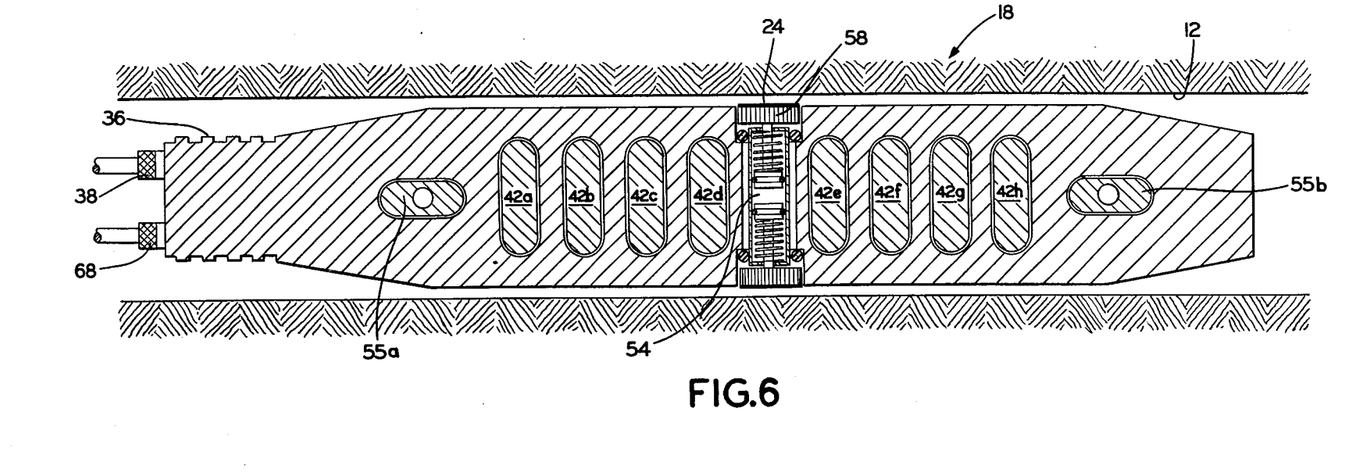
FIG. 6 is a longitudinal cross-sectional view of the jack taken at a right angle to the cross-sectional view of FIG. 5, along the plane of the pair of pistons carrying the strain gauges.

After fracturing the borehole wall, movable loading member 30 is retracted from the wall with return pistons 55a and 55b (FIGS. 5 and 6). The return pistons 55a and 55b are operated to retract loading member 30 by supplying pressurized hydraulic fluid to the third hydraulic system 75 through coupling 53. Coupling 53 communicates with return pistons 55a and 55b through line 76 (see FIG. 8).

The return pistons 55a and 55b are mounted in bores 65a and 65b (FIG. 5) and are attached to movable member 30 with pin means 67. Springs 59a and 59b seated beneath the head of return pistons 55a and 55b become compressed when the movable member 30 is operated to approach the borehole wall and assist the hydraulic pressure in line 76 in retracting the member 30 following fracturing.

Figure 8:
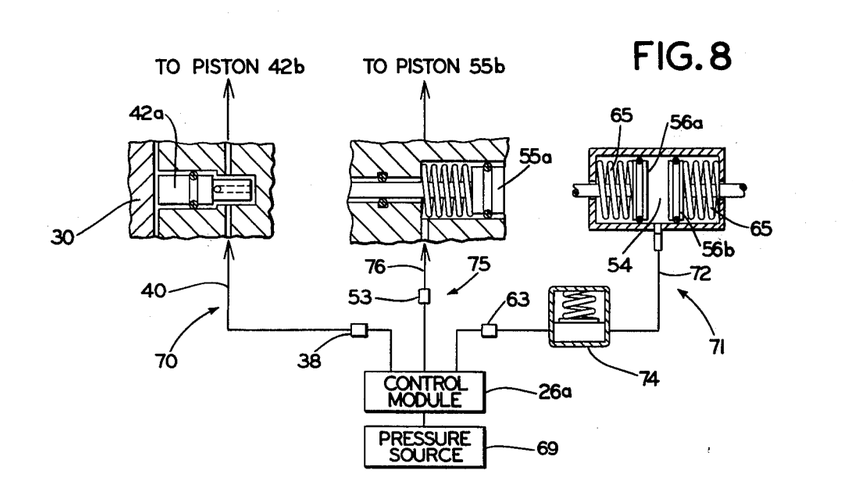
FIG. 8 is a schematic representation of the hydraulic system incorporated in the hydraulic jack.

The second hydraulic system 71 (see FIG. 8) which control piston assemblies 23a and 23b, carrying the strain gauges, includes coupling 63 for feeding hydraulic line 72. This in turn, communicates with the cylinder 54 of friction strain gauge module 24 (see also FIGS. 6 and 7). Hydraulic pressure applied to line 72 causes piston assemblies 23a and 23b to move outwardly toward the borehole wall. Once strain gauge sets 24a and 24b contact the borehole wall with adequate pressure to insure a stable output signal related to wall strain, pressure in line 72 is maintained constant by a conventional accumulator 74 (FIG. 8). This avoids the occurrence of strain gauge error caused by varying contact pressure between the gauges and borehole wall.

Referring to FIG. 7, strain gauge module 24 comprising strain gauge sets 24a and 24b is mounted to the pair of hydraulic piston assemblies 23a and 23b. The piston assemblies 23a and 23b comprise respectively piston portions 56a and 56b, piston rods 57a and 57b, and piston shoes 58a and 58b. The piston shoes 58a and 58b are pivotally mounted to piston rods 57a and 57b with ball joints to permit the shoes to automatically conform to the borehole wall. The piston portions 56a and 56b are slidably mounted within the cylinder or chamber 54, formed in double cylinder head housing 60. The housing 60 is, in turn, resiliently mounted to jack 18 with O-rings 64 to allow further accommodating movement as the shoes 58a, 58b engage the wall.

Each of the friction gauge sets 24a and 24b preferably comprises an array of friction gauges, such as the commercially available Model CBF-6 strain gauges manufactured by Tokyo Sokki Kenkujo Co., Ltd. The sets 24a and 24b are attached, respectively, to the end faces of shoes 58a and 58b of pistons or piston assemblies 23a, 23b. When hydraulic pressure is introduced into hydraulic cylinder 54 via line 72, piston portions 58a and 58b move outwardly until the strain gauge sets 24a and 24b are impressed against the borehole wall. Sufficient hydraulic pressure is maintained within the cylinder 54 to friction-bond the strain gauges to the borehole wall. As aforementioned, the shoes 58a and 58b automatically conform to the shape and orientation of the wall because they freely pivot about the ball joints of piston rods 57a and 57b. Conformation of the piston shoes 58a and 58b to the borehole wall is augmented by O-rings 64 which resiliently support the chamber housing 60 to the jack 18, and "give" somewhat as the piston shoes and strain gauges are impressed against the wall. When hydraulic pressure is removed from line 72, the piston assemblies 23a and 23b retract under the force of springs 65.

Preferably, a relatively large number of friction strain gauges are attached to the end faces of piston shoes 58a and 58b so as to obtain a large number of strain readings along the borehole wall. If desired, although not shown, the piston shoes 58a and 58b may be extended to encompass approximately 90° of the borehole wall 12, and portions of the surface of the piston shoes may be oriented non-tangentially to the wall in order to obtain shear, as well as normal, strain component readings.

Summarizing the operation of the hydraulic jack 18, in the determination of rock stress in situ in a borehole, the operator first locates the jack at the pre-selected region of a borehole (which may be either presently drilled or pre-existing) by reading the output of the three-dimensional orientation device 22 (see FIG. 1) at control panel 26. From control module 26a of control panel 26, the operator next supplies hydraulic pressure to the first hydraulic system 70 until loading members 30 and 32 come into contact with the wall of the borehole. When the contact pressure is sufficient to stabilize the jack, but without substantially loading the borehole, as determined by the back pressure registered at control panel 26, the supply of oil is stopped and the loading members 30 and 32 are locked at that hydraulic pressure.

The operator then supplies hydraulic fluid to the second hydraulic system 71 to cause pistons or piston assemblies 23a and 23b to separate until friction strain gauge sets 24a and 24b are impressed against the borehole wall. Again observing the back pressure of hydraulic fluid at control panel 26, the operator limits the supply pressure when the friction gauges are impressed against the borehole wall with a force sufficient to insure accurate strain readings.

The operator now gradually increases the hydraulic pressure in the first hydraulic system 70 to cause loading members 30 and 32 to supply an increasing loading stress to the borehole wall. Any movement of the jack as the bearing plates 30a and 32a firmly seat themselves into the borehole wall is absorbed by O-rings 64 and therefore the movement is not translated to strain gauge sets 24a and 24b.

During the entire procedure, the outputs of the strain gauge sets 24a and 24b are monitored by recorder 28. Loading of the borehole wall by loading members 30 and 32 and fracturing of the wall is observed on recorder 28 (see FIG. 4). While observing the output of recorder 28, the operator cuts off the pressure supply to the first hydraulic system 70 controlling loading members 30 and 32 just as the borehole wall fractures. However, the operator does not unload the borehole wall at this time; he waits until the output of the strain gauges monitoring the relieved strain of the wall has stabilized (see chart in FIG. 4).

The accumulator 74 assists in safeguarding against over-pressurizing the cylinder 54 of piston assemblies 23a, 23b so that the readings of strain gauge sets 24a and 24b are highly accurate. Also, as the rock fractures, any slight outward movement of the rock face is followed by the shoes 58a, 58b with the strain gauge sets 24a, 24b on the face thereof, so that the exact frictional contact is maintained and accurate reading of the de-stressed wall face is obtained.

Finally, the operator releases hydraulic pressure from both the first and second hydraulic systems 70 and 71. The piston assemblies 23a and 23b, carrying the strain gauges, withdraw under the force of springs 65. Withdrawal of the loading members 30 and 32 is provided with return pistons 55a and 55b under the force of springs 59a and 59b assisted by hydraulic pressure applied through line 76 of the third hydraulic system 75. With the loading members 30 and 32 and the piston assemblies 23a and 23b withdrawn from the borehole wall, the jack 18 is free to be relocated at another region of the borehole, or removed therefrom.

The output of the strain gauge recorder 28 (see FIG. 4) supplies data representing the initial and final strain readings of the borehole wall, as well as the change of strain of the wall with respect to borehole loading. As discussed earlier, these data are used to determine the initial state of stress of the borehole wall.

In this disclosure there is shown and described only the preferred embodiments of the invention, but, as aforementioned it is to be understood that the invention is capable of various changes or modifications within the scope of the inventive concept as expressed by the accompanying claims.

What is claimed is:

1. In situ method of measuring the natural state of stress of rock at a preselected subterranean region in a borehole, comprising the steps of:
    obtaining an initial strain reading of a test portion of the wall of said borehole at said pre-selected region, said initial strain created by the natural stress of the rock;
    de-stressing said test wall portion by creating a fracture in the wall of said borehole;
    obtaining a de-stressed strain reading of said test wall portion while maintaining open said fracture; and
    determining the natural state of stress of the rock from said initial strain and de-stressed strain readings.

2. The method of claim 1 wherein said step of determining includes the steps of determining a difference between said initial strain and de-stressed strain readings; and using said difference to determine said natural state of stress of the rock.

3. The method of claim 1 wherein said step of destressing includes the step of applying a stress to the wall of said borehole adjacent said test portion from within said borehole, said stress having a magnitude and direction sufficient to radially fracture said wall.

4. The method of claim 1 including the step of positioning a hydraulic jack having a pair of loading members into said borehole at said preselected region; and said step of de-stressing includes the step of operating said loading members to cause said fracturing adjacent said test wall portion.

5. The method of claim 1, wherein said steps of measuring include the steps of mounting a strain gauge on a movable member in said borehole in proximity to said test wall portion, actuating said movable member to move said strain gauge into firm abutment with said test wall portion; monitoring an output of said strain gauge to obtain said initial strain reading, subsequent strain readings prior to creation of said fracture in the wall of said borehole and said de-stressed strain reading of the rock; determining Young's Modulus for an assumed value of Poisson's Ratio of the rock in accordance with said subsequent strain readings whereby said determination of the natural state of stress of the rock is made with relation to said Young's Modulus; and actuating said movable member to withdraw said strain gauge from said test wall portion, so as to ready said strain gauge for a subsequent strain reading.

6. In situ method of measuring natural state of stress of rock at a preselected subterranean region, comprising the steps of:
    drilling a borehole into said rock extending into said preselected region;
    positioning a hydraulic jack into said borehole at said preselected region;
    obtaining an initial strain reading of a test portion of the wall of said borehole in proximity to said hydraulic jack;
    applying a stress to said wall with said hydraulic jack adjacent said test wall portion, said stress being of sufficient magnitude and direction to create a radial fracture in the surface of said wall to de-stress said test wall portion;
    obtaining a de-stressed strain reading of said test wall portion while maintaining open said fracture; and
    using said initial strain and said de-stressed strain readings to determine the natural state of stress of said rock.

7. The method of claim 6 wherein said steps of measuring include the steps of mounting a strain gauge on a movable member, actuating said member to move said gauge into abutment with said test wall portion; monitoring an output of said strain gauge to obtain said initial strain and de-stressed strain readings; and then activating said member to withdraw said gauge from said test wall portion, said strain gauge being readied for a subsequent strain measurement.

8. In situ method of measuring the natural stress of rock at a preselected subterranean region of a borehole comprising the steps of:
    positioning a jack having a pair of loading members into said borehole at said preselected region;
    initially separating said loading members against opposite quadrants of said borehole for stabilizing said jack;
    impressing strain gauges against the remaining quadrants of said borehole with a constant impressing pressure;
    monitoring outputs of said strain gauges to obtain an initial strain reading of the rock caused by the natural state of stress thereof;
    further separating said stressing members to form a fracture in the wall of said borehole;
    monitoring outputs of said strain gauges while maintaining open said fracture with said loading members to obtain a de-stressed strain reading of the rock; and
    determining the natural state of stress of the rock using said initial strain and de-stressed strain readings.

9. In situ method of measuring the natural state of stress of rock at a preselected subterranean region, comprising the steps of:
    drilling a borehole into said rock extending into said preselected region;
    positioning a jack into said borehole at said preselected region, said jack having first and second pairs of oppositely movable members, said second pair of members carrying strain gauges;
    initially separating said first pair of members against opposite quadrants of said borehole for stability;
    separating said second pair of members to firmly impress said strain gauges against the remaining quadrants of said borehole;
    monitoring outputs of said strain gauges to obtain an initial strain reading of the rock caused by the natural state of stress thereof;
    further separating said first pair of members to form a fracture of said borehole;
    monitoring outputs of said strain gauges while maintaining open said fracture with said first members to obtain a de-stressed strain reading of the rock;
    withdrawing said first and second pairs of movable members, said jack being movable to another preselected region of said borehole; and
    determining the natural state of stress of the rock using said initial strain and said de-stressed strain readings.

10. Instrumentation for determining borehole rock stress in situ including an adjustable jack structure, extendible means traversing said borehole and by connection to said jack structure enabled to facilitate operative disposition of said jack structure in said borehole, a control module and data recording means remotely situated from said jack structure, and means operatively communicating said remote module and recording means with said jack structure, wherein said jack structure comprises, a movable member complementally disposed with respect to a stationary member to form an extended body section of said jack structure wherein to each said member is affixed a plate adapted to bear upon a surface of said borehole, a plurality of jointly acting pistons operatively arranged in said stationary member and integrally connected with said movable member such that upon pressure applied thereto said jointly acting pistons displace said movable member with respect to said stationary member whereby said plates are brought into contact with opposite surfaces of said borehole, a chamber traversing said body member in a perpendicular direction with respect to a longitudinal axis of said borehole, a double cylinder head housing flexibly disposed in said chamber, oppositely directed piston assemblies operatively arranged in said housing with each including a piston rod extending from said housing and directed toward further opposite surfaces of said borehole, a piston shoe flexibly mounted on each said piston rod, and a strain gauge set operatively arranged on a surface of each said piston shoe facing said borehole surface and adapted to respond to pressure applied thereto upon activation of said piston assemblies whereby said piston shoes are driven to engage said surfaces thereof with said borehole surfaces, a plurality of piston drive control systems whereof each said system operates in response to direction from said control module, including a first said system controlling said action of said jointly acting pistons, and a second said system controlling said activation of said piston assemblies, and means communicating responses from said strain gauge sets to said recording means upon activation of said piston assemblies.

11. Instrumentation as set forth in claim 10, further comprising a movable member return piston means operatively disposed in said stationary member and connected to said movable member, said return piston means being adapted to act in opposition to said action of said jointly acting pistons, and said drive control systems including a third said system controlling said action of said movable member return piston means.

12. Instrumentation as set forth in claim 10 wherein a plurality of apertured flexible mounting elements are spatially disposed in said body member chamber, and said cylinder head housing is supported within elements.

13. Instrumentation as set forth in claim 10 wherein said controlled drive of said piston shoes is perpendicularly directed with respect to said controlled displacement of said movable member.

14. Instrumentation as set forth in claim 10 wherein a pivotal connection flexibly mounts to each said piston rod said piston shoe therefor.

* * * * *